US00PP29321P3

(12) United States Plant Patent
Wallace

(10) Patent No.: US PP29,321 P3
(45) Date of Patent: May 29, 2018

(54) *CEANOTHUS* PLANT NAMED 'MATCEA01'

(50) Latin Name: *Ceanothus griseus*
Varietal Denomination: MATCEA01

(71) Applicant: Ryan Wallace, Sacramento, CA (US)

(72) Inventor: Ryan Wallace, Sacramento, CA (US)

(73) Assignee: Matsuda of Green Acres, Inc., Sacramento, CA (US)

( * ) Notice: Subject to any disclaimer, the term of this patent is extended or adjusted under 35 U.S.C. 154(b) by 55 days.

(21) Appl. No.: 14/999,517

(22) Filed: May 18, 2016

(65) Prior Publication Data

US 2017/0339808 P1 Nov. 23, 2017

(51) Int. Cl.
*A01H 5/00* (2018.01)
*A01H 5/02* (2018.01)
*A01H 5/12* (2018.01)

(52) U.S. Cl.
USPC ..... Plt./226
CPC ..... *A01H 5/02* (2013.01); *A01H 5/12* (2013.01)

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Ceanothus* cultivar named 'MATCEA01' is disclosed, characterized by distinctive dark green foliage with a yellow margin. Plants exhibit good tolerance to high heat and sun, resisting leaf scorch. Plants are vigorous and grow rapidly reaching approximately 10 feet in diameter and 2 feet tall at approximately 2 years in favorable landscape conditions. The new cultivar is a *Ceanothus*, suitable for ornamental garden purposes.

1 Drawing Sheet

Latin name of the genus and species: *Ceanothus griseus*.
Variety denomination: 'MATCEA01'.

BACKGROUND OF THE INVENTION

The new cultivar is a product of chance discovery by the inventor Ryan Wallace. This new variety, hereinafter referred to as 'MATCEA01', was discovered as a naturally occurring single branch mutation of *Ceanothus griseus* 'Diamond Heights', unpatented. The discovery and selection of the new variety was made during July of 2014. The new variety was selected by the inventor at a commercial nursery in Sacramento, Calif.

After identifying the new variety as a potentially interesting selection, the inventor first organized propagation of 'MATCEA01' by vegetative terminal cuttings September of 2014 at the same commercial nursery in Sacramento, Calif. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'MATCEA01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MATCEA01' These characteristics in combination distinguish 'MATCEA01' as a new and distinct *Ceanothus* cultivar:

1. Unique dark green foliage with yellow margins.
2. Vigorous growth habit, reaching mature size quickly.
3. Observed resistance to leaf scorch in direct sun.
4. Finished plant size of approximately 2 feet tall and 10 feet wide.

COMPARISON TO PARENT VARIETY

'MATCEA01' is similar in most horticultural characteristics to the parent *Ceanothus griseus* 'Diamond Heights'. Plants of the new cultivar 'MATCEA01' however differ in the following:

1. The new variety has dark green foliage with a yellow margin; parent variety has yellow foliage with a green center blotch
2. The new variety resists leaf scorch under full sun conditions, as found in Sacramento, Calif., where the parent variety has been observed to suffer from leaf scorch.
3. Finished plant size of the new variety is approximately 2 feet tall and 10 feet wide, finished plant size of the parent is approximately 1 foot tall and 6 feet wide.
4. Plants of the new variety are more vigorous and grower faster, as well as larger than plants of the parent variety.

COMMERCIAL COMPARISON

'MATCEA01' can be compared to the commercial variety *Ceanothus griseus horizontalis* 'Yankee Point' unpatented. Plants of the new cultivar 'MATCEA01' are similar to plants of 'Yankee Point' in most horticultural characteristics, especially plant form, however, plants of the new cultivar 'MATCEA01' differ in the following:

1. 'MatCea01' has foliage with a yellow margin; foliage of this comparator is solid green.
2. Plants of 'Yankee Point' require shade in very warm Summer climates, plants of 'MatCea01' aren't tolerant of full sun conditions in very warm Summer climates.

'MATCEA01' can be compared to the commercial variety *Ceanothus thyrsifolus griseus* 'Perado', U.S. Plant Pat. No. 13,433. Plants of the new cultivar 'MATCEA01' are similar to plants of 'Perado' in some horticultural characteristics, including variegated foliage. Plants of the new cultivar 'MATCEA01' however, differ in the following;

1. Plants of the new variety are semi-prostrate, plants of 'Perado' are upright globular.
2. Plants of the new variety reach a height of approximately 2 feet, plants of 'Perado' grow to approximately 8 feet tall.
3. Plants of the new variety are much denser than the open form of 'Perado'.
4. Plants of 'Perado' require shade in very warm Summer climates, plants of 'MatCea01' aren't tolerant of full sun conditions in very warm Summer climates.
5. Plants of the new variety are faster growing than plants of 'Perado'.

BRIEF DESCRIPTION OF THE PHOTOGRAPH

The accompanying photograph in FIG. 1 illustrates in full color a close up of typical flowers and foliage of the new variety. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MATCEA01' plants grown outdoors in Loxley, Ala. Plants are approximately 1 year old, in a 3 gallon nursery container. Measurements and numerical values represent averages of typical plant types.

Botanical classification: *Ceanothus griseus* 'MATCEA01'.

PROPAGATION

Typically by semi-hardwood cuttings in Spring and Summer.

Rooting: Approximately 1 month at 18° C. to initiate rooting. Approximately 3 months 18° C. to produce a rooted cutting.

Root description: Fine, fibrous young roots, well branched. Colored near RHS Grey-Brown 199A.

PLANT

Growth habit: Prostrate, trailing, evergreen shrub.

Height: Approximately 17 to 18 cm to top of foliar and flowering plane, in a 3 gallon pot at approximately 1 year old.

Plant spread: Approximately 80 cm.

Branching characteristics: Well branched, approximately 4 to 8 primary branches from the center of the plant. Branches occur at approximately 15° to 45° angles. Each primary branch has 6 to 10 lateral branches.

Primary branches:

Length of primary branches: Average range 25 to 40 cm.

Diameter of primary branches: Approximately 0.5-0.8 cm.

Primary branch strength: Moderately strong and flexible.

Primary branch color: Near RHS Green 138A.

Primary branch texture: Glabrous, ridged.

Lateral branches:

Number of lateral branches: Approximately 6 to 10 per primary branch.

Length of lateral branches: Average range 10 to 20 cm.

Diameter of lateral branches: Average 0.4 cm.

Lateral branch strength: Moderately strong and flexible.

Lateral branch color: Near RHS Green 137C.

Lateral branch texture: Glabrous, ridged.

Internode length: Average 2.0 to 2.8 cm.

Age of plant described: Approximately 1 year.

FOLIAGE

Leaf:

*Type*.—Simple.

*Arrangement*.—Opposite.

*Average length*.—Approximately 3.5 to 4.7 cm.

*Average width*.—Approximately 2.0 to 2.5 cm.

*Shape of blade*.—Ovate.

*Apex*.—Broad acute.

*Base*.—Truncate.

*Attachment*.—Stalked.

*Margin*.—Finely and irregularly serrate or crenate.

*Texture of top surface*.—Glabrous.

*Texture of bottom surface*.—Glabrous.

*Color*.—Young foliage upper side: Near RHS Green 139A margin near Green 138A and Yellow-Green 144C. Young foliage under side: Near RHS Green 137B margin near Yellow-Green 144B. Mature foliage upper side: Near RHS Green 139A margin near Yellow 3C. Mature foliage under side: Near RHS Green 137B margin near Yellow-Green 144B.

*Venation*.—Type: Pinnate. Three main parallel veins, with laterals occurring in a pinnate pattern. Venation color upper side: Near RHS Green 137A. Venation color under-side: Near RHS Yellow-Green 144C.

*Petiole*.—Length: About 0.8 cm. Diameter: About 0.2 cm. Color: Upper Surface: Near RHS Green 137C. Lower Surface: Near RHS Yellow-Green 144B.

FLOWER

Bloom period: Plants begin flowering in the late Winter to very early Spring, and continues for approximately 4 to 6 weeks.

Flower: Campanulate, monecious, outwardly facing flowers arranged in a raceme.

Inflorescence:

*Height*.—Average 3.5 to 5.0 cm.

*Diameter*.—Average 3.0 cm.

*Shape*.—Obconical.

*Flowers per*.—50 to 70.

Individual flowers:

*Length*.—Average 0.3 cm.

*Diameter*.—Average 0.3 cm.

Petals:

*Length*.—Approximately 0.2 cm.

*Width*.—Approximately 0.1 cm.

*Apex*.—Rounded.

*Shape of petal*.—Spatulate.

*Petal margin*.—Entire. Aspect very slightly undulating.
*Petal arrangement*.—Single whorl.
*Petal number*.—5 full petals. 3 to 5 irregularly shaped and sized petaloids in center of flower.
*Petal texture*.—Smooth, glabrous all surfaces.

Color:
*Upper surface at first opening*.—Near RHS Violet-Blue 97B.
*Under surface at first opening*.—Near RHS Violet-Blue 97C.
*Inner surface at maturity*.—Near Violet-Blue 97B.
*Outer surface at maturity*.—Near RHS Blue 101D.
*Upper surface at fading*.—Near RHS Violet-Blue 97D.
*Under surface at fading*.—Near RHS Blue 106D.

Peduncle:
*Length*.—Average 0.5 cm to 2.5 cm.
*Diameter*.—0.2 cm.
*Color*.—Near RHS Green 138A.
*Texture*.—Glabrous.
*Aspect*.—Straight.
*Strength*.—Moderately sturdy and flexible.

Pedicel:
*Length*.—Average 0.5 cm.
*Diameter*.—0.1 cm.
*Color*.—Near RHS Green 138A.
*Texture*.—Glabrous.
*Aspect*.—Straight. Angle of attachment, approximately 15 to 45°.
*Strength*.—Soft and flexible.

Bud:
*Shape*.—Globular.
*Length*.—0.2 cm.
*Diameter*.—0.3 cm.
*Color*.—Near RHS Violet-blue 98D.

Calyx/sepals:
*Quantity per flower*.—5 sepals.
*Shape*.—Ovate.
*Length*.—0.2 cm.
*Width*.—0.1 cm.
*Apex*.—Acute.
*Base*.—Truncate.
*Margin*.—Entire.
*Texture*.—Glabrous all surfaces.
*Color*.—Inner Surface: Near RHS Yellow-Green 145B, flushed Violet-Blue 94C.
*Outer Surface*.—Near RHS Yellow-Green 145B, flushed Violet-Blue 94D.

REPRODUCTIVE ORGANS

Stamens:
*Number*.—5.
*Stamen length*.—0.3 cm.
*Width*.—Less than 0.1 cm.
*Color*.—Near RHS White N155A.

Anthers:
*Length*.—Approximately 0.1 cm.
*Shape*.—Linear.
*Color*.—Near RHS Yellow 6D.
*Pollen*.—Scant, colored near Yellow 14D.

Pistil:
*Number*.—1.
*Length*.—Average 0.5 cm.
*Style*.—Length: Average 0.4. Color: Near RHS White N155A.
*Stigma*.—Globular, colored near Yellow-White 158A.
*Ovary*.—Approximately 1 mm in diameter, colored near Black 202B.

OTHER CHARACTERISTICS

Disease and pest resistance: Not observed to be susceptible nor resistant to normal diseases and pests of *Ceanothus*.
Temperature tolerance: Hardy to approximately 20 to 25° F. Tolerant of high temperatures to approximately 100° F.
Fruit/seed production: Not observed to date.

What is claimed is:

1. A new and distinct cultivar of *Ceanothus* plant named 'MATCEA01' as herein illustrated and described.

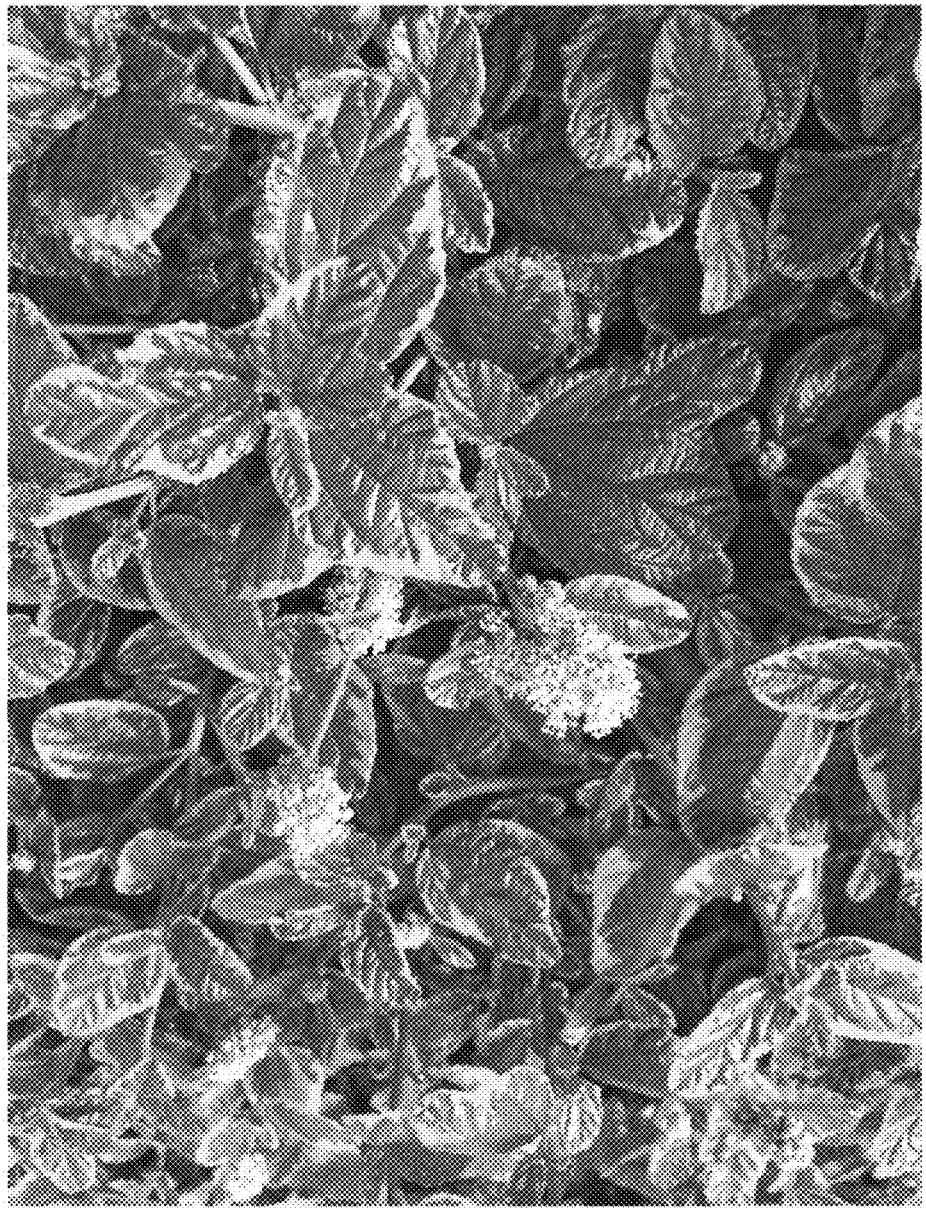

* * * * *